(12) United States Patent
Breit et al.

(10) Patent No.: US 7,919,084 B2
(45) Date of Patent: Apr. 5, 2011

(54) METHODS OF DIAGNOSIS, PROGNOSIS AND TREATMENT OF CARDIOVASCULAR DISEASE

(75) Inventors: Samuel N. Breit, New South Wales (AU); David A. Brown, New South Wales (AU)

(73) Assignee: St. Vincent's Hospital Sydney Limited, New South Wales (AU)

(*) Notice: Subject to any disclaimer, the term of this patent is extended or adjusted under 35 U.S.C. 154(b) by 458 days.

(21) Appl. No.: 11/600,839

(22) Filed: Nov. 17, 2006

(65) Prior Publication Data
US 2007/0077598 A1    Apr. 5, 2007

Related U.S. Application Data

(62) Division of application No. 10/172,497, filed on Jun. 17, 2002, now Pat. No. 7,157,235.

(51) Int. Cl.
*A61K 39/395* (2006.01)
(52) U.S. Cl. .................. 424/130.1; 424/158.1; 514/1.9
(58) Field of Classification Search .................. None
See application file for complete search history.

(56) References Cited

U.S. PATENT DOCUMENTS
2003/0113744 A1* 6/2003 O'Toole et al. ............... 435/6

FOREIGN PATENT DOCUMENTS
| | | |
|---|---|---|
| EP | 0904292 | 3/1999 |
| JP | 07250688 | 10/1995 |
| JP | 07258293 | 10/1995 |
| WO | WO 94/03599 | 2/1994 |
| WO | WO 95/14772 | 6/1995 |
| WO | WO 96/18730 | 6/1996 |
| WO | WO 97/00958 | 1/1997 |
| WO | WO 99/06445 | 2/1999 |
| WO | WO 00/70051 | 11/2000 |
| WO | WO 01/81928 A1 | 11/2001 |

OTHER PUBLICATIONS

Xu et al., Circ. Res., 2006, vol. 98:342-350.*
Brown et al; The LANCET, Jun. 22, 2002, vol. 359:2159-2163.
Sidney et al; Circulation 1998, vol. 98(11): pp. 1058-1063.
Bootcov et al; Proc Natl Acad Sci USA 1997, vol. 94(21): pp. 11514-11519.
Yudkin et al; Atherosclerosis 2000, vol. 148(2): pp. 209-214.
Hak et al; Atherosclerosis 2000, vol. 149(1): pp. 163-168.
Zhu et al; Am J Cardiol. 2000, vol. 85(2): pp. 140-146.
Database EMBL Online, Accession No. R33078 (XP002199768).
Yokoyama-Kobayashi, M. et al; Human cDNA Encoding a Novel . . . Expressed in Placenta[1]; J. Biochem., vol. 122, pp. 622-626 (1997).
Lawton, L.N., et al; "Identification of a novel member of the TGF-beta superfamily highly expressed in human placenta"; Gene; vol. 203; pp. 17-26 (1997).
Hillier, S.L.; "The Relationship of Amniotic Fluid Cytokines . . . Histologic Chorioamnionitis, and Chorioamnion Infection"; Obstetrics and Gynacology, vol. 81; pp. 941-948 (1993).
Hromas, R. et al; "PLAB, a novel placental bone morphogenetic protein"; Biochimica et Biophysica Acta, vol. 1354; pp. 40-44 (1997).
Paralkar, V. et al; "Cloning and Characterization of a Novel Member . . . Morphogenetic Protein Family"; J. Biol. Chem, vol. 273, issue 22, pp. 13760-13767 (1998).
Moore, A.G. et al; "The Transforming Growth Factor-β Superfamily . . . in the Serum of Pregnant Women"; The Journal of Clinical Endocrinology & Metabolism, vol. 85, No. 12, pp. 4781-4788 (2000).
Fairlie, W.D. et al; "MIC-1 is a Novel TGF-β Superfamily Cytokine Associated with Macrophage Activation"; Journal of Leukocyte Biology, vol. 65, pp. 2-5 (1999).
Bootcov, M.R. et al; "MIC-1, a Novel Microphage Inhibitory Cytokine, is a Divergent Member of the TGF-β Superfamily"; Proc. Natl. Acad. Sci. USA, vol. 94, pp. 11514-11519 (1997).
Strelau, J. et al; "GDF-15/MIC-1 a Novel Member of the TGF-β Superfamily"; Journal of Neural Transmission; Supplementum 60; Advances in Research on Neurodegeneration, vol. 8; pp. 273-276 (2000).
Strelau, J. et al; "Growth/Differentiation Factor-15/Macrophage . . . Dopaminergic Neurons in Vivo"; The Journal of Neuroscience, vol. 20 (23); pp. 8597-8603 (2000).
Bottner, M. et al; "Characterization of the Rat, Mouse, and Human Genes of . . . Inhibiting Cytokine-1 (GDF-15/MIC-1)"; Gene; vol. 237, pp. 105-111 (1999).
Bottner, M. et al; "Expression of a Novel Member of the TGF-β Superfamily . . . Cytokine-1 (GDF-15/MIC-1) in Adult Rat Tissues"; Cell and Tissue Research, vol. 297, pp. 103-110 (1999).
Baoutina, A. et al; "Antioxidant Properties of Macrophages Toward Low-Density Lipoprotein"; TCM, vol. 11(1), pp. 1-7 (2001).
Ross, R.; "Atherosclerosis—An Inflammatory Disease"; N. England J. Med.; vol. 340 No. 2; pp. 115-126 (1999).
Ridker, P.M. et al; "Plasma Concentration of Interleukin-6 and the Risk of . . . Apparently Healthy Men"; Circulation, vol. 101(15); pp. 1767-1772 (2000).
Ridker, P.M. et al; "C-Reactive Protein and Other Markers of Inflammation in the Prediction of Cardiovascular Disease in Women"; N. England J. Med.; vol. 342 No. 12; pp. 836-843 (2000).

* cited by examiner

*Primary Examiner* — Elizabeth C. Kemmerer
*Assistant Examiner* — Xiaozhen Xie
(74) *Attorney, Agent, or Firm* — Nixon & Vanderhye

(57) ABSTRACT

The invention provides methods for diagnosis or prognosis of cardiovascular disease involving the detection of an elevated amount of MIC-1 in a test body sample. The invention also provides methods for treatment of cardiovascular disease and other chronic inflammatory disease.

2 Claims, 4 Drawing Sheets

FIGURE 4 (A) A

METHODS OF DIAGNOSIS, PROGNOSIS AND TREATMENT OF CARDIOVASCULAR DISEASE

This application is a divisional of application Ser. No. 10/172,497, filed Jun. 17, 2002, now U.S. Pat. No. 7,157,235, the entire content of which is hereby incorporated by reference in this application.

FIELD OF THE INVENTION

This invention relates to the field of medical diagnostics. In particular, the invention provides methods for diagnosis or prognosis of cardiovascular disease. The invention also provides methods for treatment of cardiovascular disease and other chronic inflammatory diseases.

BACKGROUND TO THE INVENTION

Macrophage Inhibitory Cytokine 1 (MIC-1) is a TGF-β superfamily protein first cloned on the basis of increased mRNA expression associated with macrophage activation (1). While MIC-1 is not expressed in resting macrophages, stimulation of macrophages by a number of biological mediators including TNF-α, IL-1 and M-CSF induce MIC-1 expression. Because of its induction by many pro-inflammatory cytokines, but failure of direct induction by lipopolysaccharide and interferon gamma, it has been hypothesised that MIC-1 may be an autocrine down-regulator of macrophage activation (1).

Although originally identified in activated macrophages, MIC-1 can be expressed in several tissues (2-5). Northern blots of human tissues indicate the presence of small amounts of MIC-1 mRNA in the kidney, pancreas and prostate, and large amounts in the placenta (2, 4). Large amounts of MIC-1 have also been detected by immunohistochemistry in biopsies of breast, colon and prostate cancer (5). However, MIC-1 is not detectable within normal epithelial cells of these organs (5). This, along with induction of MIC-1 expression by p53 and data suggesting that MIC-1 is able to induce apoptosis of some epithelial tumour cells lines (6-8), also suggests a role for MIC-1 in epithelial neoplasms.

Shortly after cloning MIC-1 cDNA, two allelic forms of this gene existing due to a single nucleotide polymorphism were identified. This polymorphism causes an alteration of a histidine (H) to an aspartic acid (D) residue at position 6 of the mature MIC-1 protein (9). The homozygous D allele is present in about 5% of normal individuals (10). Because the properties of these amino acids differ from each other, it was hypothesised that this may lead to alteration in some aspect of the function of the MIC-1 protein. In the course of undertaking epitope-mapping studies of a series of monoclonal and polyclonal anti-MIC-1 antibodies, it became apparent that one of these antibodies was able to discriminate between the H and D alleles (9), a property which allows the deduction of the genotype from the phenotype of the MIC-1 protein present in serum (10). These antibodies have also allowed the development of a sensitive immunoassay capable of quantifying MIC-1 in normal and pathological sera (2).

As MIC-1 is a product of activated macrophages, the present inventors considered that serum or plasma measurement of MIC-1 may be diagnostically and/or prognostically informative of cardiovascular disease, particularly atherosclerosis, since there is a wide body of data implicating activated macrophages in the pathogenesis of atherosclerosis and in the vascular occlusion that is often the ultimate end point of this process (11, 12). There is also strong epidemiological data linking measurement of inflammatory markers such as C-reactive protein (CRP) and IL-6 with the risk of vascular occlusive events (13, 14). The work presented hereinafter demonstrates that the typical increased inflammatory response present within atherosclerotic vessel walls is associated with increased secretion and release of MIC-1 and that the consequent increase in basal levels of MIC-1 is associated with an increased risk of future cardiovascular events.

SUMMARY OF THE INVENTION

Thus, in a first aspect, the present invention provides a method of diagnosis or prognosis of cardiovascular disease, the method comprising detecting an elevated amount of MIC-1 in a test body sample from a subject.

In a second aspect, the method provides a method of treatment of cardiovascular disease in a subject said method comprising administering to said subject an effective amount of an agent which inhibits the activity or expression of MIC-1.

In a third aspect, the present invention provides a method of treatment of cardiovascular disease in a subject, said method comprising administering to said subject an effective amount of an agent which enhances or increases the activity or expression of MIC-1.

In a fourth aspect, the present invention provides a method of treatment of chronic inflammatory disease in a subject, said method comprising administering to said subject an effective amount of an agent as defined in either of the second or third aspects.

DETAILED DISCLOSURE OF THE INVENTION

In a first aspect, the present invention provides a method of diagnosis or prognosis of cardiovascular disease, the method comprising detecting an elevated amount of MIC-1 in a test body sample from a subject.

Preferably, the cardiovascular disease is atherosclerosis.

Preferably, the elevated amount of MIC-1 in the test body sample is detected by:

(i) determining the amount of MIC-1 present in the said test body sample; and (ii) comparing said amount of MIC-1 against an amount or a range of amounts of MIC-1 present in comparative body sample(s) taken from healthy subject(s).

The amount of what may be regarded as an "elevated amount" of MIC-1 may vary according to the particular body sample type used. The preferred body sample is a sample of blood plasma, however a sample of amniotic fluid, placental extract, whole blood, serum, buffy coat, urine, cerebrospinal fluid, seminal fluid, synovial fluid, or a tissue biopsy may also be suitable. For blood plasma, an amount of >600 pg/ml is likely to represent an elevated amount of MIC-1 which indicates, in a statistically significant manner, cardiovascular disease (including development of vascular plaques) and/or a likelihood of a future cardiovascular event (eg myocardial infarction, thromboembolic stroke, or cardiovascular death). An amount of MIC-1 of >850 pg/ml in a blood serum sample is likely to represent an elevated amount of MIC-1 which strongly indicates cardiovascular disease and/or a very high likelihood of a future cardiovascular event. The future cardiovascular event indicated by an elevated amount of MIC-1 in a body sample may occur within 1 to 4 years following the taking of the test sample.

The amount of MIC-1 present in a body sample may be readily determined by, for example, immunoassays or immunohistochemistry (eg with sectionalised samples of a tissue biopsy) using anti-MIC-1 antibodies or fragments thereof.

Anti-MIC-1 antibodies and fragments thereof may be produced by any of the methods well known in the art.

Preferably, the subject is female and/or >45 years of age.

The results obtained by the method of the first aspect of the present invention may be combined with the results of assays of other known cardiovascular disease biomarkers (eg CRP and/or IL-6 (13, 14)) as well as an assessment(s) of other cardiovascular disease risk factors (eg obesity, smoking habit, hypertension, hyperlipidemia, familial history of premature cardiovascular disease, and diabetes), to improve diagnostic and/or prognostic accuracy.

The results obtained by the method of the first aspect of the present invention may be particularly useful in;

(i) predicting risk of catastrophic vascular occlusions in the heart, brain, limbs or other regions;

(ii) predicting alteration to the risk mentioned in (i) arising from treatment with beneficial agents (eg statins);

(iii) predicting, in the context of subjects experiencing acute chest pair, those subjects requiring urgent treatment;

(iv) predicting, in the context of subjects experiencing stable angina those subjects likely to develop serious cardiovascular events;

(v) predicting, in the context of subjects experiencing unstable angina, those subjects likely to experience a myocardial infarction;

(vi) predicting, in the contexts of subjects experiencing a myocardial infarction, the risk of early cardiovascular events such as recurrent heart attacks and cardiovascular death; and (vii) predicting, in the context of subjects who have undergone a successful angioplasty stenting procedure, the likelihood of poor, long term results such as restenosis and/or additional cardiac symptoms.

Virtually all people develop the first lesions (the "fatty streak") of vascular disease early in life (15), and these may evolve into typical plaques which progress through various stages, from the relatively simple structure of the fatty streak with accumulation of modified lipids, to the stable or sometimes unstable plaques of advanced atherosclerosis (16). The evolution of these lesions revolves around a complex interplay between the vascular endothelium, vascular smooth muscle, and the immune system. The principal response of the immune system is migration of macrophages and T-cells to the vascular intimal space, after recruitment by the activated endothelium. The local production of cytokines directs plaque evolution and induces migration of vascular smooth muscle cells, among other cell types, in an attempt to contain and stabilise the vascular injury (16). Many factors are involved in the generation of an unstable atherosclerotic plaque as opposed to the stable fibrotic plaque. Among these, the regulation and interaction between the macrophage, vascular smooth muscle and tissue matrix is paramount. Continued macrophage activation results in delayed resolution of vascular injury and contributes to the release of mediators which influence vascular smooth muscle and tissue matrix (17). Apoptosis of vascular smooth muscle, changes in metaloproteinase activity and secretion and neovascularisation all contribute to destabilization of the plaque (17, 18). In animal models, plaque instability has been shown to be induced by up-regulation of p53 (18). Transcription of MIC-1 mRNA is also induced by p53 (6-8) and in some cells, the expression of MIC-1 is related to increased expression of the cell cycle related protein $p21^{ap1/waf1}$, metaloproteinases and cell adhesion associated proteins. Increased metaloproteinase production has also been associated with the development of plaque instability (17). These associations, in concert with the work presented hereinafter, suggest that MIC-1 may represent a novel target for cardiovascular disease treatment.

Thus, in a second aspect, the present invention also provides a method of treatment of cardiovascular disease in a subject, said method comprising administering to said subject an effective amount of an agent which inhibits the activity or expression of MIC-1.

Preferably, the agent utilised in the method of the second aspect is selected from anti-MIC-1 antibodies and fragments thereof and other agents which inhibit or block MIC-1 activity (eg MIC-1 fragments which block receptor binding, and antibodies which bind to MIC-1 receptors to block MIC-1 binding). Alternatively, the agent is selected from antisense RNA (or DNA constructs for expression of antisense RNA) or ribozymes (or DNA constructs for expression of ribozymes) targeted to the MIC-1 gene, or DNAzymes targeted to the MIC-1 gene or other agents which inhibit or block expression of MIC-1. DNA constructs encoding anti-MIC-1 antisense RNAs or ribozymes may be administered to the subject by any of the methods well known to the art, for example, by the use of recombinant adenoviral or adenoviral-associated vectors or by linking an antisense RNA-encoding or ribozyme-encoding DNA sequence to an appropriate promoter sequence to produce a linear DNA molecule for administration within a liposome. The agent may also be a DNA construct which encodes a dominant negative mutation of the MIC-1 gene. The agent may be administered by any of the methods well known in the art, for example, oral, nasal, intravenous and intramuscular administration. The agent may be administered as a composition comprising a pharmaceutically-acceptable carrier(s) and/or excipient(s).

In a third aspect, the present invention provides a method of treatment of cardiovascular disease in a subject, said method comprising administering to said subject an effective amount of an agent which enhances or increases the activity or expression of MIC-1.

Preferably, the agent utilised in the method of the third aspect is selected from MIC-1, functional fragments thereof, MIC-1 mimetic compounds, and other agents which enhance or increase the activity or expression of MIC-1.

MIC-1 may be obtained by purification from a suitable source (eg blood taken from humans or other animals) or produced by standard recombinant DNA techniques such as is described in, for example, Maniatis, T. et al., Molecular Cloning: a laboratory manual, Second Edition, Cold Spring Harbor Laboratory Press. Recombinant MIC-1 may incorporate modifications (eg amino acid substitutions, deletions, and additions of heterologous amino acid sequences), which may, for example, enhance biological activity or expression of the protein. However, preferably, the method of the third aspect utilises human MIC-1. The MIC-1 may also be glycosylated by methods well known in the art and which may comprise enzymatic and non-enzymatic means.

Suitable functional fragments of MIC-1 may be produced by cleaving purified natural or recombinant MIC-1 with well known proteases such as trypsin and the like, or more preferably, by recombinant DNA techniques or peptide/polypeptide synthesis. Such functional fragments may be identified by generating candidate fragments and assessing biological activity. Preferably, functional fragments will be of 5 to 100 amino acids in length, more preferably, of 10 to 30 amino acids in length. The functional fragments may be linear or circularised and may include modifications of the amino acid sequence of the native MIC-1 sequence from whence they are derived (eg amino acid substitutions, deletions, and additions of heterologous amino acid sequences). The functional fragments may also be glycosylated by methods well known in the art and which may comprise enzymatic and non-enzymatic means.

Suitable MIC-1 mimetic compounds (ie compounds which mimic the function of MIC-1) may be designed using any of the methods well known in the art for designing mimetics of peptides based upon peptide sequences in the absence of secondary and tertiary structural information (Kirshenbaun, T, Zuckermann, R. N., and Dill, K. A. 1999 Designing polymers that mimic biomolecules. *Curr Opin Stract Biol* 9:530-535). For example, peptide mimetic compounds may be produced by modifying amino acid side chains to increase the hydrophobicity of defined regions of the peptide (eg substituting hydrogens with methyl groups on aromatic residues of the peptides), substituting amino acid side chains with non-amino acid side chains (eg substituting aromatic residues of the peptides with other aryl groups), and substituting amino- and/or carboxy-termini with various substituents (eg substituting aliphatic groups to increase hydrophobicity). Alternatively, the mimetic compounds may be so-called peptoids (ie non-peptides) which include modification of the peptide backbone (ie by introducing amide bond surrogates by, for example, replacing the nitrogen atoms in the backbone with carbon atoms), or include N-substituted glycine residues, one or more D-amino acids (in place of L-amino acid(s)) and/or one or more α-amino acids (in place of β-amino acids or γ-amino acids). Further mimetic compound alternatives include "retro-inverso peptides" where the peptide bonds are reversed and D-amino acids assembled in reverse order to the order of the L-amino acids in the peptide sequence upon which they are based, and other non-peptide frameworks such as steroids, saccharides, benzazepine1,3,4-trisubstituted pyrrolidinone, pyridones and pyridopyrazines. Suitable mimetic compounds may also be designed/identified by structural modelling/determination, by screening of natural products, the production of phage display libraries (Sidhu, S. S., Lowman, H. B., Cunningham, B. C., and Wells, J. A. 2000 Phage display for selection of novel binding peptides. *Methods Enzymol* 328:333-363), minimised proteins (Cunningham, B. C., and Wells, J. A. 1997 Minimized proteins. *Carr Opin Struct Biol* 7:457-462), SELEX (Aptamer) selection (Drolet, D. W., Jenison, R. D., Smith, D. E., Pratt, D., and Hicke, B. J. 1999 A high throughout platform for systematic evolution of ligands by exponential enrichment (SELEX). *Comb Chem High Throughout Screen* 2:271-278), combinatorial libraries and focussed combinatorial libraries, virtual screening/database searching (Bissantz, C., Folkers, G., and Rognan, D. 2000 Protein-based virtual screening of chemical databases. 1 Evaluation of different docking/scoring combinations. *J Med Chem* 43:4759-4767), and rational drug design techniques well known in the art (Houghtee, R. A, Wilson, D. B., and Pinilla, C. 2000 Drug Discovery and vaccine development using mixture-based synthetic combinatorial libraries. *Drug Discovery Today* 5:276-285).

The agent utilised in the method of the third aspect may also be a DNA construct encoding MIC-1 or a functional fragment thereof which may be administered to the subject by any of the methods well known to the art, for example, by the use of recombinant adenoviral or adenoviral-associated vectors or by linking a MIC-1-encoding or MIC-1 functional fragment-encoding DNA sequence to an appropriate promoter sequence to produce a linear DNA molecule for administration within a liposome. The agent may be administered by any of the methods well known in the art, for example, oral, nasal, intravenous and intramuscular administration. The agent may be administered as a composition comprising a pharmaceutically-acceptable carrier(s) and/or excipient(s).

In addition to cardiovascular disease, it is considered that other chronic inflammatory diseases will be beneficially treated with an agent as defined in either the second or third aspects.

Thus, in a fourth aspect, the present invention provides a method of treatment of chronic inflammatory disease (eg rheumatoid arthritis, Alzheimer's disease, multiple sclerosis, chronic active hepatitis, primary biliary cirrhosis, encephalitis, meningitis, chronic viral hepatitis (ie as caused by Hepatitis B and Hepatitis C viruses), drug or alcohol induced hepatitis, sarcoidosis, pulmonary fibrosis, Guillaine Barre syndrome, systemic lupus erythematosus, Crohn's disease, ulcerative collitis, Reiter's syndrome, seronegative arthritis or spondylitis, vasculitis, cardiomyopathy, uveitis, sunburn, psoriasis, exczema, nephritis, pneumonitis, Sjogren's syndrome, and scleroderma) in a subject, said method comprising administering to said subject an effective amount of an agent as defined in either of the second or third aspects.

The terms "comprise", "comprises" and "comprising" as used throughout the specification are intended to refer to the inclusion of a stated step, component or feature or group of steps, components or features with or without the inclusion of a further step, component or feature or group of steps, components or features.

Any discussion of documents, acts, material, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

The invention will hereinafter be described by way of the following non-limiting examples and accompanying figures.

BRIEF DESCRIPTION OF THE ACCOMPANYING FIGURES

EXAMPLE 1

Patients and Method

Figure 1:
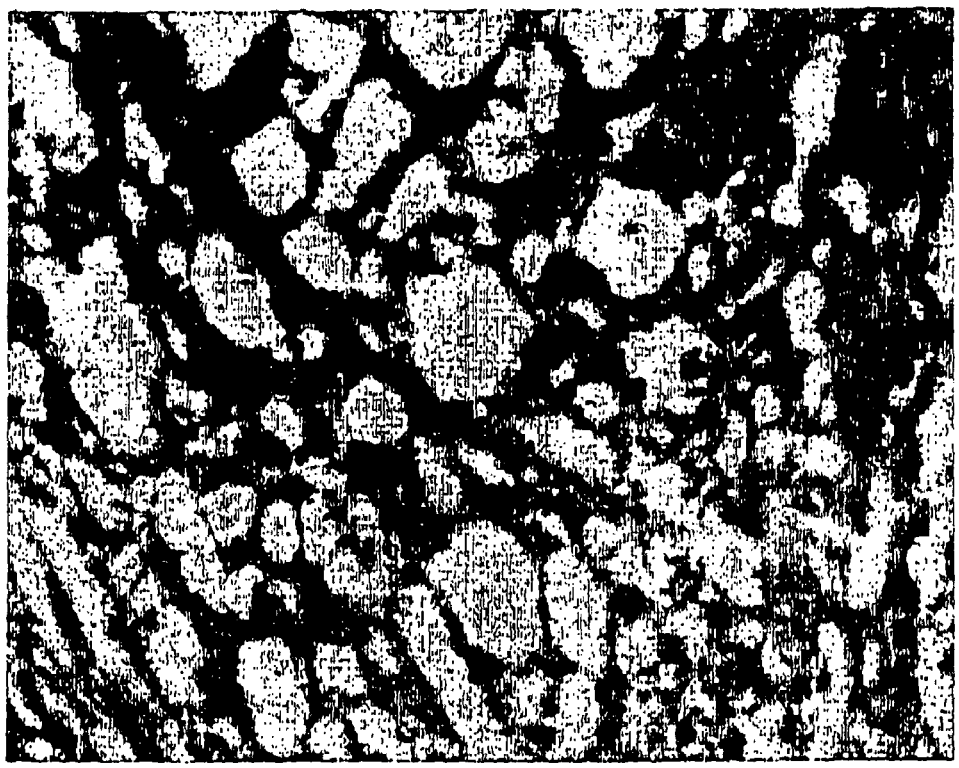
FIG. 1 shows aortic sections from a stage II atherosclerotic patient stained with anti-MIC-1 antibody (A) and a control antibody (B).
Figure 1:
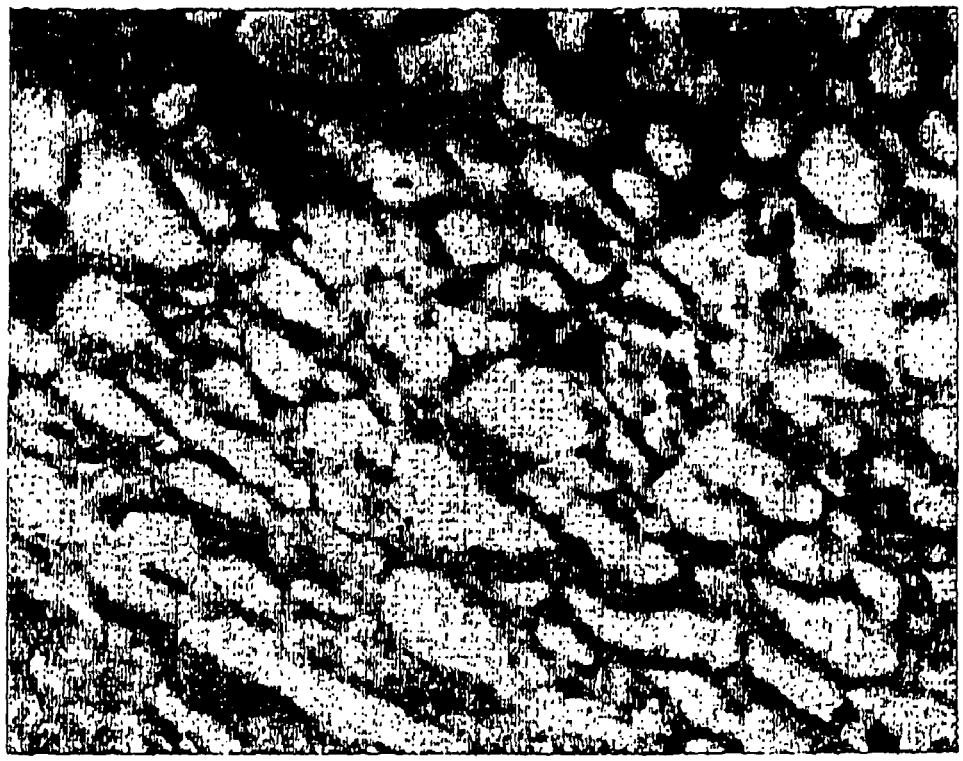

A prospective, nested case-control study was conducted among apparently healthy women participating in the Women's Health Study (WHS), an ongoing primary prevention trial of aspirin and vitamin E being conducted among 27,628 American women aged 45 and over, with no prior evidence of cardiovascular disease or cancer (19). Each study participant provided a baseline plasma and buffy coat sample which has been stored on liquid nitrogen until the time of analysis. Methods used for the collection, storage, and retrieval of these samples were as described previously (14, 19). As part of routine follow-up in the WHS, all study participants provided detailed baseline clinical information regarding usual cardiovascular risk factors, and on a biannual basis were contacted for evidence of incident medical disorders.

For the purposes of this analysis, case women were those, WHS participants who provided baseline blood samples and subsequently developed myocardial infarction, thromboembolic stroke, or cardiovascular death during an initial 4-year follow-up period. As described elsewhere (14, 19), the endpoint of myocardial infarction was confirmed if review of medical records demonstrated diagnostic symptom patterns, ECG changes, and cardiac enzyme elevations, while the diagnosis of thromboembolic stroke was based upon evidence of new-onset neurological symptoms lasting greater than 24 hours with diagnostic CT or MRI scan imaging. The diagnosis of cardiovascular death was confirmed using additional information from hospital records, autopsy reports, and family contact.

For each study participant who developed a confirmed study endpoint, one control study participant was selected at random from those women who also provided a baseline blood sample and who remained free of reported cardiovascular events during follow-up. This control participant was matched to the case participant for age (within one year) and smoking status (never, past, current). Using these methods, 257 confirmed cases were matched with 257 controls and this formed the basis for the nested case-control evaluation.

Procedures

Baseline blood samples from each case-control pair were analysed for both plasma levels of MIC-1 and for polymorphism in the MIC-1 gene, using methods described previously (2, 10). In brief, total MIC-1 plasma concentration was determined using a sandwich ELISA with mouse monoclonal, anti-hMIC-1 antibody 26G6H6 (International Patent Application No. PCT/AU01/00456 (WO 01/81928)) for antigen capture. Samples were diluted 1:10 in antibody diluent (1% BSA w/v, 0.05% TWEEN 20 v/v in PBS). Following a 1-hour incubation of the samples with immobilised capture antibody, the plates were washed and 100 μl/well of the detection antibody 233B-P (International Patent Application No. PCT/AU01/00456 (WO 01/81928)) was then added at a dilution of 1:25,000 (v/v). This r incubated at 4° C. for 16 hours then washed. This was followed by the addition of 100 μl/well of a biotinylated donkey anti-sheep antibody (Jackson's Immunoresearch). After incubation for 1 hour, the plates were washed and 100 μl/well of 1:2,000 dilution of streptavidin was added for 30 minutes. Colour development proceeded with the addition of 100 μl/well of OPD (0.4 mg/ml w/v). This reaction was terminated with 4N sulfuric acid and the plates were read at 490 nm (Pasteur diagnostic). The hMIC-1 plasma concentration was determined by reference to a standard curve that was constructed using recombinant hMIC-1 protein.

The genotype of a plasma sample was deduced from the phenotype using an ELISATYPE assay essentially as previously described (10). This was based on the ratio of the plasma level determined with 13C4H4 (International Patent Application No. PCT/AU01/00456 (WO 01/81928)) as capture antibody to that determined with 26G6H6 as capture antibody. Mouse monoclonal, anti-hMIC-1 13C4H4 has a much stronger affinity to the H allele than the D allele of MIC-1 protein, whilst 26G6H6 detects both alleles with equally affinity (9). As has been previously determined, a ratio of less than zero signifies a homozygous DD individual, between zero and 0.5 a heterozygous HD individual, and a ratio of greater than 0.7 a homozygous HH individual (10). Human serum samples representing the three genotypes, previously characterised by DNA sequencing, were used as controls in both assays. Sample diluent was used as a background control. All samples were assayed in triplicate.

Statistical Analysis

Clinical characteristics at study entry of the case and control subjects were compared using either the Students' t-test or chi-square analysis, while matched t-tests were used to compare mean levels of MIC-1 between the two study groups. The inventors sought to evaluate for any evidence of association between MIC-1 and subsequent vascular risk in models assuming both linear and non-linear effects. Thus, case and control subjects were first divided into quartiles on the basis of the control distribution of plasma MIC-1, and then conditional logistic regression analyses were employed to assess for any evidence of risk across increasing quartiles of MIC-1 concentration. Then, to explore for threshold effects, similar regression analyses were used to assess for evidence of risk associated with basal MIC-1 levels above or below pre-specified cut-points of the MIC-1 distribution at the $50^{th}$, $75^{th}$, $90^{th}$, and $95^{th}$ percentile of the control distribution, In all of these analyses, case and control subjects were matched on age and smoking status, and additionally controlled for randomised assignment to aspirin and/or vitamin E. To assess for independent effects, additional analyses were performed which further controlled for body mass index, hypertension, hyperlipidemia, family history of premature coronary disease, diabetes, and exercise frequency. In addition, evidence was sought to show that MIC-1 might provide additional prognostic information when compared to C reactive protein (CRP). This was achieved by dividing study participants into four groups on the basis of CRP and MIC-1 levels above or below the study median for each parameter. Relative risks of future vascular events were then computed using those with below median values for both parameters as the referent. Finally, chi-square analysis was used to address whether gene frequencies of the MIC-1 polymorphism differed between cases and controls, as well as logistic regression analysis to calculate relative risks associated with carriership of the MIC-1 polymorphism. In all analyses, 95% confidence intervals and 2-sided P-values were computed.

Results

Of the 257 incidents of cardiovascular events evaluated in this prospective study, 111 represented myocardial infarction, 113 thromboembolic stroke, and 33 cardiovascular death. As expected, women who subsequently developed these events during follow-up (cases) were more likely than their matched controls to have a personal history of hyperlipidemia, hypertension obesity, or diabetes. There were no differences between groups in terms of hormone replacement therapy usage. Due to the study design, cases and controls were virtually identical in terms of age and smoking status (Table 1).

Overall, mean MIC-1 levels were higher at baseline among women who developed cardiovascular events compared to those who did not (685 versus 578 pg/ml, P<0.001). In crude age and smoking matched analyses, assuming a linear relationship between basal MIC-1 levels and incident vascular disease, each quartile increase in MIC-1 was found to be associated with a 35 percent increase in risk of future cardiovascular events (95% CI 16 to 58%, P=0.0001). Specifically, the relative risks of future vascular events from lowest (referent) to highest quartiles of baseline MIC-1 were 1.0, 0.94, 1.33, and 2.32. These findings were minimally attenuated and remained statistically significant after additional controls were added for body mass index, diabetes, hypertension, hyperlipidemia, exercise frequency, and a family history of premature coronary artery disease (Table 2). In analyses exploring for evidence of a threshold effect, the highest risks were found to be associated with the very highest levels of baseline MIC-1. Furthermore, those women with baseline MIC-1 levels above the 90$^{th}$ percentile of the control distribution (>856 pg/ml) had a nearly three fold increase in risk compared to those with lower levels (RR=2.7, 95% CI 1.64-4.95, P=0.001)(Table 3). As might be expected, modest positive correlations were observed between basal levels of MIC-1 and log normalised basal levels of both IL-6 (r=0.35, P=0.001) and CRP (r=0.22, P=0.002). However, the observed relationships between MIC-1 and incident vascular disease were only marginally attenuated after additional adjustment for these inflammatory biomarkers. By contrast, there was evidence that the predictive value of MIC-1 added to that of CRP. Specifically, compared to those with levels of MIC-1 and CRP below the study median, those with levels of both these parameters above the study median had a relative risk of 4.3 (95% CI 2.0 to 9.1, P=0.001). This risk estimate was greater than that associated with elevation of either MIC-1 or CRP alone.

As shown in Table 4, the overall gene frequencies for the MIC-1 polymorphism were in Hardy Weinberg equilibrium (HH=54.3%, HD=40.9%, DD=4.9%). However, no evidence was found for a difference in either gene frequencies or allele frequencies for the MIC-1 polymorphism between cases and controls (both P values >0.7) such that the relative risk of future events for carriers of the polymorphic D allele compared to non-carriers was 0.93 (95% CI 0.65 to 1.31, P=0.7). Despite the finding of higher MIC-1 levels among cases than among controls, no evidence was found to indicate that allele status per se significantly affected MIC-1 levels.

TABLE 1

Baseline characteristics of study participants.

|  | Controls N = 257 | Cases N = 257 | P* |
|---|---|---|---|
| Age (years) | 60.2 | 60.2 | * |
| Smoking Status (%) |  |  | * |
| Current | 22.2 | 22.2 |  |
| Past | 42.4 | 42.4 |  |
| Never | 35.4 | 35.4 |  |
| Body Mass Index (kg/m2) | 25.5 | 27.0 | 0.001 |
| 0.001 |  |  |  |
| Hyperlipidemia (%) | 33.9 | 43.6 | 0.02 |
| Hypertension (%) | 31.3 | 56.7 | 0.001 |
| 0.001 |  |  |  |
| Family History CAD (%) | 13.8 | 17.0 | 0.3 |
| Diabetes (%) | 2.0 | 12.8 | 0.001 |
| 0.001 |  |  |  |
| HRT use (%) | 38.9 | 40.5 | 0.7 |

*Matching variables.
HRT = hormone replacement therapy.
CAD = coronary artery disease

TABLE 2

Numbers of study participants and relative risks (RR) of developing future cardiovascular events among apparently healthy women, according to baseline quartiles of MIC-1.

|  | Quartile of MIC-1 (range) | | | | |
|---|---|---|---|---|---|
|  | 1 (<431) | 2 (431-531) | 3 (532-670) | 4 (>670) | P |
| Controls, N (%) | 64 (24.9) | 64 (24.9) | 65 (25.3) | 64 (24.9) |  |
| Cases, N (%) | 46 (17.9) | 43 (16.7) | 62 (24.1) | 106 (41.3) |  |
| RR, crude* | 1.00 | 0.94 | 1.33 | 2.32 | 0.0001 |
| 95% CI | — | 0.55-1.61 | 0.79-2.32 | 1.42-3.78 |  |

TABLE 2-continued

Numbers of study participants and relative risks (RR) of developing future cardiovascular events among apparently healthy women, according to baseline quartiles of MIC-1.

|  | Quartile of MIC-1 (range) | | | | |
|---|---|---|---|---|---|
|  | 1 (<431) | 2 (431-531) | 3 (532-670) | 4 (>670) | P |
| P | — | 0.8 | 0.3 | 0.0008 |  |
| PR, adjusted* | 1.00 | 0.75 | 1.19 | 1.97 | 0.003 |
| 95% CI | — | 0.41-1.36 | 0.68-2.09 | 1.15-3.37 |  |
| P | — | 0.3 | 0.5 | 0.01 |  |

*All models matched on age and smoking status. Crude RR adjusted for randomised treatment assignment to aspirin and vitamin E; adjusted RR additionally controlled for body mass index, exercise frequency, family history of coronary disease before age 60, and a personal history of diabetes, hyperlipidemia, or hypertension.

TABLE 3

Numbers of study participants and relative risks (RR) of developing future cardiovascular events among apparently healthy women, according to baseline MIC-1 above or below pre-specified percentile cutpoints of the study distribution.

| Cut-point | MIC-1 | Controls, N (%) | Cases, N (%) | RR* | 95% CI | P |
|---|---|---|---|---|---|---|
| 50$^{th}$ | >531 | 129 (50.2) | 165 (65.4) | 1.88 | 1.31-2.67 | 0.0005 |
| 75$^{th}$ | >670 | 64 (25.0) | 106 (41.3) | 2.13 | 1.45-3.10 | 0.0001 |
| 90$^{th}$ | >856 | 26 (10.1) | 60 (23.4) | 2.70 | 1.64-4.95 | 0.0001 |
| 95$^{th}$ | >1003 | 13 (5.1) | 32 (12.5) | 2.66 | 1.36-5.21 | 0.004 |

*Matched for smoking and age, and adjusted for randomised treament assignment

TABLE 4

Gene frequencies for the MIC-1 polymorphism, overall and according to case or control status.

| Genotype | Overall (N = 514) | Cases (N = 257) | Controls (N = 257) | P |
|---|---|---|---|---|
| HH | 54.3 | 55.2 | 53.3 | 0.8 |
| HD | 40.9 | 40.5 | 41.2 |  |
| DD | 4.9 | 4.3 | 5.5 |  |
| HH | 54.3 | 55.2 | 53.3 | 0.7 |
| HD or DD | 45.7 | 44.8 | 46.7 |  |

Discussion

In this prospective cohort of apparently healthy middle-aged American women, it was found that baseline levels of MIC-1 were elevated among those at increased risk for developing future cardiovascular events. Specifically, women with the highest levels of MIC-1 at entry had a relative risk of future myocardial infarction, thromboembolic stroke, or cardiovascular death nearly three times that of women with lower levels of MIC-1 at entry. While MIC-1 levels were found to correlate with both IL-6 and CRP (two other inflammatory biomarkers known to predict risk in this cohort (14)), adjustment for these factors only modestly attenuated the overall findings. It is considered that these findings for MIC-1 indicate that the determination of elevated MIC-1 levels in a body sample are useful for diagnosis or prognosis of cardiovascular disease.

EXAMPLE 2

MIC-1 Immunolocalisation within Atherosclerotic Blood Vessels

Methods, Results and Discussion

Atherosclerotic vessel sections from patients and APO-E gene knockout mice (20) were reacted with either polyclonal sheep anti-MIC-1 antibody or a control sheep antibody. The antibodies were diluted 1 in 2000 in PBS-Triton with 2% FBS using standard methods. Following washes, the sections were treated with peroxidase-labelled anti-sheep antibody and the areas of labelling visualised using DAB.

Figure 2:
FIG. 2 shows aortic sections from a stage IV atherosclerotic patient stained with anti-MIC-1 antibody (A) and a control antibody (B).
Figure 2:
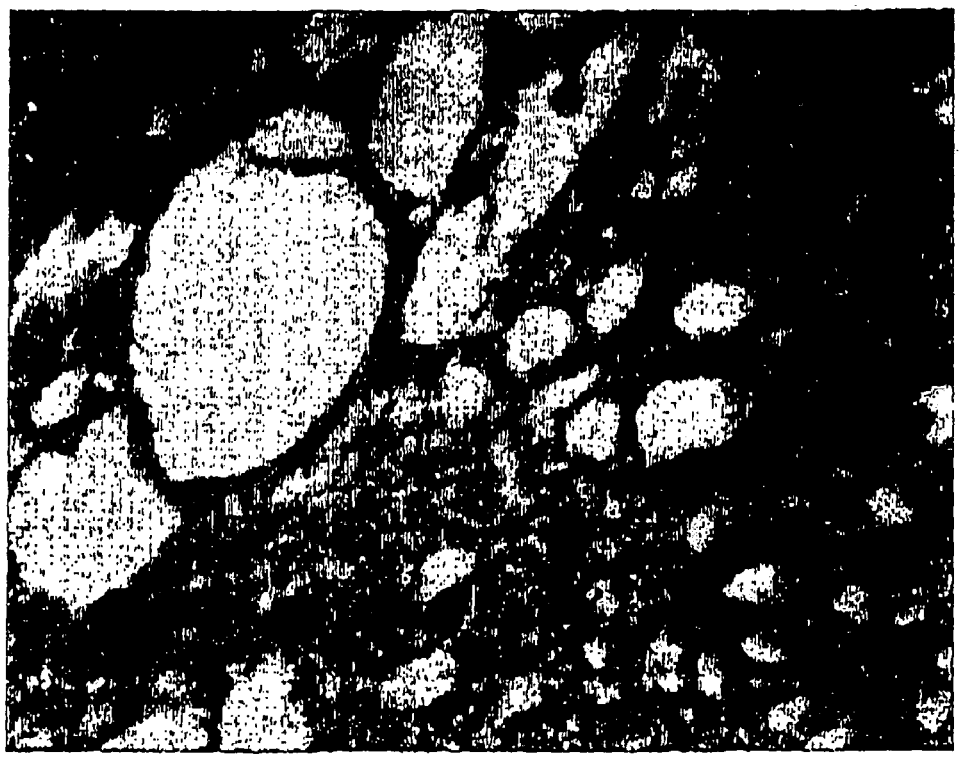
Figure 3:
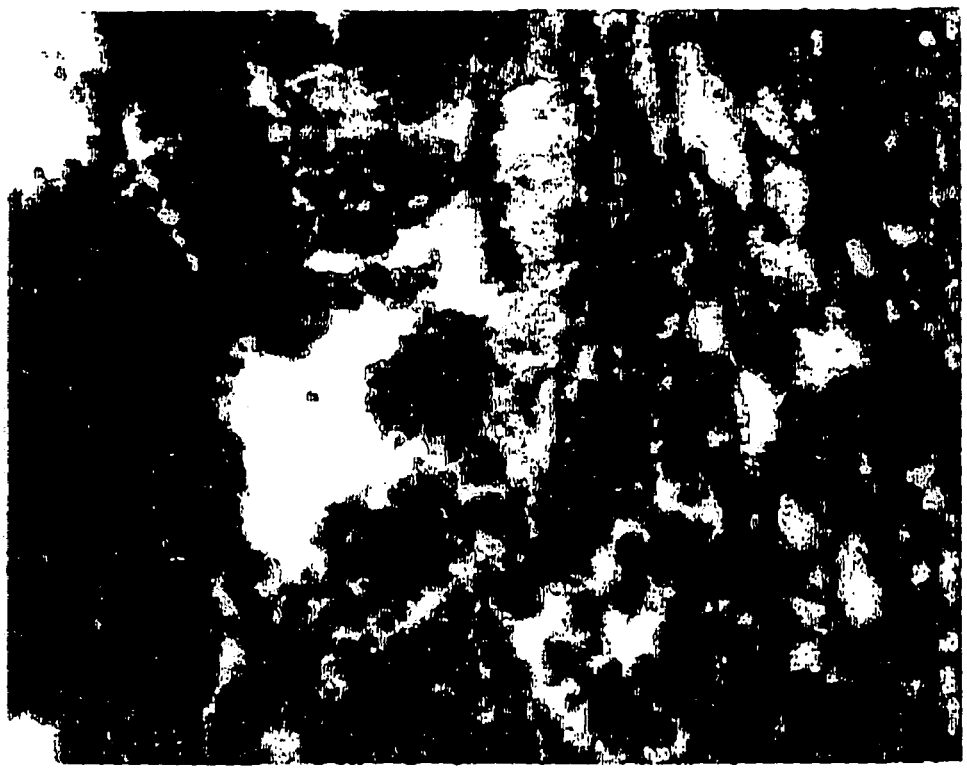
FIG. 3 shows necrotic aortic sections from a stage IV atherosclerotic patient stained with anti-MIC-1 antibody (A) and a control antibody (B).
Figure 3:
Figure 4:
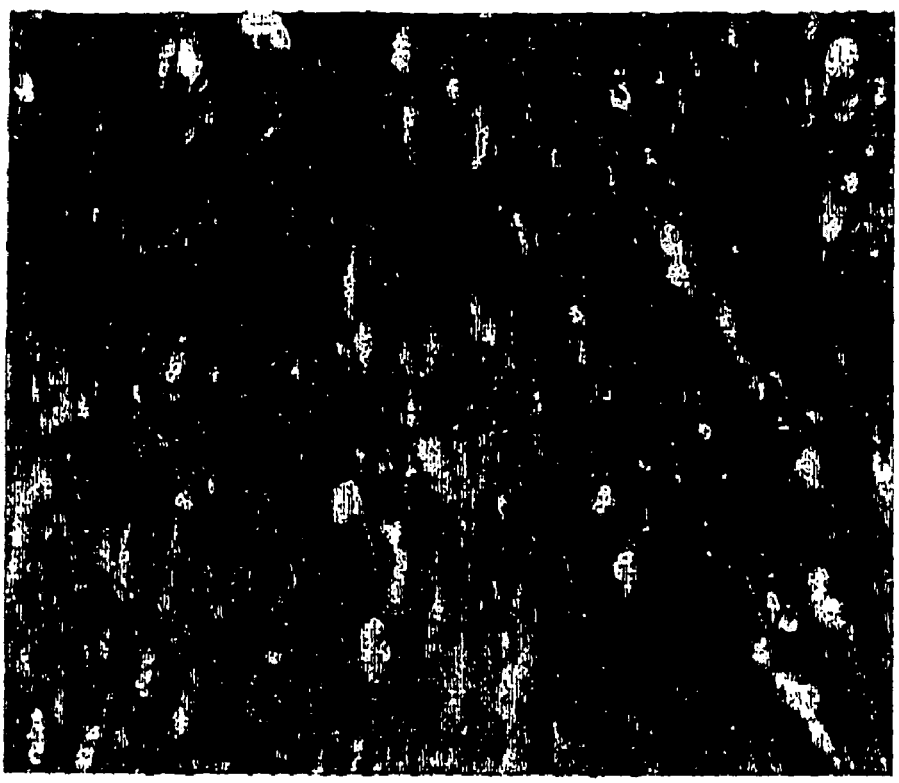
FIG. 4 shows an atherosclerotic aorta section from an atherosclerosis-prone mouse (ie an Apo-E gene knockout) stained with anti-MIC-1 antibody (A) and a control antibody (B).
Figure 4:
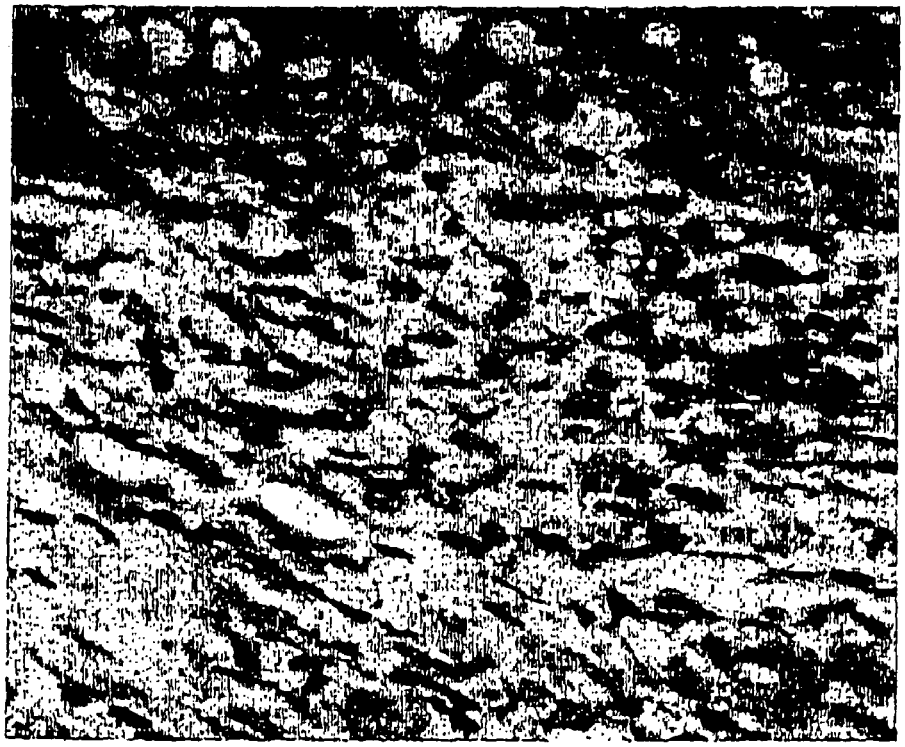

Both experimental atherosclerotic aortas from Apo-E gene knockout mice (FIGS. 1 to 4) and early and late stage atherosclerotic tissues from patients were positive to anti-MIC-1 immunostaining. MIC-1 immmunoreactive cells were mainly confined to the lesioned sub-endothelium at stage I (21). Significant proportions of endothelial cells, foam cells and smooth muscle cells were immmunoreactive to MIC-1 at each layer at stages II (FIG. 1) and III. As lesions progress to stage IV (FIG. 2), the majority of the cells positively stained with anti-MIC-1. Furthermore, the necrotic core (FIG. 3) of the atheromatous plaque was very strongly stained.

It will be appreciated by persons skilled in the art that numerous variations and/or modifications may be made to the invention as shown in the specific embodiments without departing from the spirit or scope of the invention as broadly described. There present embodiments are, therefore, to be considered in all respects as illustrative and not restrictive.

REFERENCES

1. Bootcov M R, Bauskin A R, Valenzuela S M, Moore A G, Bansal M, He X Y, et al. MIC-1, a novel macrophage inhibitory cytokine, is a divergent member of the TGF-beta superfamily. Proc Natl Acad Sci USA 1997; 94(21):11514-9.
2. Moore A G, Brown D A, Fairlie W D, Bauakin A R, Brown P K, Munier M L, et al. The transforming growth factor-beta superfamily cytokine macrophage inhibitory cytokine-1 is present in high concentrations in the serum of pregnant women. J Clin Endocrinol Metab 2000; 85(12): 4781-8.
3. Bottner M, Suter-Crazzolara C, Schober A and Unsicker K Expression of a novel member of the TGF-beta superfamily, growth/differentiation factor-15/macrophage-inhibiting cytokine-1 (GDF-15/MIC-1) in adult rat tissues. Cell Tissue Res 1999, 297(1):103-10.
4. Fairlie W D, Moore A G, Bauskin A R, Russell P K, Zhang H P and Breit S N. MIC-1 is a novel TGF-beta superfamily cytokine associated with macrophage activation. J Leukoc Biol 1999; 65(1):2-5.
5. Brown D A, Liu T, Ward R L, Hawkins N J, Fairlie W D, Bauskin A R, et al. Macrophage inhibitory cytokine-1 (MIC-1) in epithelial neoplasia. Submitted.
6. Li P X Wong J. Ayed A, Ngo D, Brade A M, Arrowsmith C, Austin R C and Klamut H J. Placental transforming growth factor-beta is a downstream mediator of the growth arrest and apoptotic response of tumor cells to DNA damage and p53 overexpression. J Biol Chem 2000; 275(26):20127-35.
7. Kannan K, Amariglio N, Rechavi G, and Givol D. Profile of gene expression regulated by induced p53: connection to the TGF-beta family. FEBS Lett 2000; 470(1):77-82.
8. Tan M, Wang Y, Guan K and Sun Y. PTGF-beta, a type beta transforming growth factor (TGF-beta) superfamily member, is a p53 target gene that inhibits tumor cell growth via TGF-beta signalling pathway. Proc Natl Acad Sci USA 2000; 97(1):109-14.
9. Fairlie W D, Russell P K, Wu W M, Moore A G, Zhang H P, Brown P K, et al. Epitope mapping of the transforming growth factor-beta superfamily protein, macrophage inhibitory cytokine-1 (MIC-1): identification of at least five distinct epitope specificities. Biochemistry 2001; 40(1):65-73.
10. Brown D A, Fairlie W D, Bauskin A R Liu T, Xu N, Smith M D, et al. ELISATYPE: A novel approach to high volume genotyping for MIC-1 polymorphism. Clin Chem 2001 (in review).
11. Baoutina A, Dean R T, and Jessup W. Antioxidant properties of macrophages toward low-density lipoprotein Trends Cardiovasc 2001; 11(1):1-7.
12. Ross R. Atherosclerosis—an inflammatory disease. N Engl J Med 1999; 340:115-26.
13. Ridker P M, Rifai N, Stampfer M J and Hennekens C H. Plasma concentration of interleukin-6 and the risk of future myocardial infarction among apparently healthy men. Circulation 2000; 101(15):1767-72.
14. Ridker P M, Hennekens C H, Buring J E and Rifai N. C-reactive protein and other markers of inflammation in the prediction of cardiovascular disease in women. N Engl J Med 2000; 342(12):836-43.
15. Stary H C, Chandler A B, Glagov S, Guyton J R, Insull W Jr, Rosenfeld M E, et al. A definition of initial, fatty streak, and intermediate lesions of atherosclerosis. A report from the Committee on Vascular Lesions of the Council on Arteriosclerosis, American Heart Association. Arterioscler Thromb 1994; 14(5):840-56.
16. Tegos T J, Kalodiki E, Sabetai M M and Nicolaides A N. The genesis of atherosclerosis and risk factors: a review. Angiology 2001; 52(2):89-98.
17. Mayer M and Xu Q. Smooth muscle cell apoptosis in arteriosclerosis. Exp Geront 2001; 36: 969-87.
18. Von der Thusen T H, Van Vlijmen B J, Streefland M, Biessen E A and Van Berkel T J. Alteration of carotid atherosclerotic plaque composition in apo E −/− mice by adenoviral transfer of p53. J. Subricros. Cytol Pathol 2000; 32(S016): 328.
19. Buring J E and Hennekens C H. The Women's Health Study: summary of the study design. J Myocard Ischemia 1992; 4(27-9).
20. Plump A S, Smith J D, Hayek T, Aalto-Setala K, Walsh A, Verstuyft J G, Rubin E M and Breslow J L. Severe hypercholesterolemia and atherosderosis in apolipoprotein E-deficient mice created by homologous recombination in ES cells. Cell 1992; 71:34-53).
21. Stary H C, Chandler A B, Dinsmore R E, Fuster V, Glagov S, Insull W J, Rosenfeld M E, Schwartz C J, Wagner W D and Wissler R W. A definition of advanced types of atherosclerotic lesions and a histological classification of atherosclerosis. A report from the Committee on Vascular Lesions of the Council on Arteriosclerosis, American Heart Association. Arterioscl Thromb Vasc Biol 1995, 15:1512-1531.

The invention claimed is:

1. A method of treatment of atherosclerosis in a subject afflicted with the disease, said method comprising administering to said subject an effective amount of an agent which inhibits the activity of Macrophage Inhibitory Cytokine-1 (MIC-1), wherein the agent is an anti-MIC-1 antibody or antigen-binding fragment thereof.

2. The method of claim 1, wherein the agent is administered as a composition comprising a pharmaceutically-acceptable carrier or excipient.

* * * * *